United States Patent [19]

Barthelemy et al.

[11] Patent Number: 4,847,344

[45] Date of Patent: Jul. 11, 1989

[54] HEAT-RESISTANT MALEIMIDO COPOLYMERS

[75] Inventors: Pascal Barthelemy, Lyon; Yves Camberlin, Caluire, both of France

[73] Assignee: Rhone-Poulenc Chimie, Courbevoie, France

[21] Appl. No.: 166,482

[22] Filed: Mar. 10, 1988

[30] Foreign Application Priority Data

Mar. 10, 1987 [FR] France .................................. 87 03513

[51] Int. Cl.$^4$ .............................................. C08F 10/00
[52] U.S. Cl. ...................................... 526/262; 526/279; 525/103; 528/21; 528/24; 528/26; 528/27; 528/38
[58] Field of Search ................ 526/262, 279; 525/103; 528/26, 27, 38, 24, 21

[56] References Cited

U.S. PATENT DOCUMENTS 4,544,728 10/1985 Dien et al. ............................ 528/27
4,656,235 4/1987 Tesoro et al. ....................... 528/279

Primary Examiner—Melvyn I. Marquis
Attorney, Agent, or Firm—Burns, Doane, Swecker & Mathis

[57] ABSTRACT

Novel heat-resistant maleimido polymers, well adopted for the production of molded/laminated shaped articles, are copolymerizates of (a) a hydrocarbyl N,N'-bis(-maleimide); (b) a diamine containing a diorganopolysiloxane bridge; optionally, (c) an N,N'-bis(-maleimide) containing a diorganopolysiloxane bridge; optionally, (d) at least one other comonomer copolymerizable therewith; and, optionally, (e) a catalyst therefor.

12 Claims, No Drawings

HEAT-RESISTANT MALEIMIDO COPOLYMERS

CROSS-REFERENCE TO RELATED APPLICATION

Our copending application, Ser. No. 166,501, filed on 3/10/88 and assigned to the assignee hereof.

BACKGROUND OF THE INVENTION

1. Field of the Invention:

The present invention relates to novel heat-resistant polymers which are copolymerizates of bis(maleimides), optionally including a bis(maleimide) containing a diorganopolysiloxane bridge in its molecular structure, and diamines comprising a diorganopolysiloxane bridge. This invention also relates to the preparation of such polymers.

2. Description of the Prior Art:

It is known to this art (see French Patent FR-A-1,555,564) that heat resistant polymers may be prepared by reacting an N,N'-bis(imide) of an unsaturated dicarboxylic acid, such as, for example, an N,N'-bis(maleimide) with certain aromatic diprimary diamines. These polymers, which exhibit exceptional heat resistance, may be used for the manufacture of molded parts, laminates or shaped articles, with a view to the widest diversity of applications.

SUMMARY OF THE INVENTION

It has now been found that polymers can be produced which have, among other properties, a high impact strength, by reacting one or more N,N'-bis(maleimides) of the type described in the aforementioned '564 patent with an aromatic diprimary diamine containing a diorganopolysiloxane bridge in its molecular structure, optionally in the presence of an N,N'-bis(maleimide) also containing a diorganopolysiloxane bridge in its molecular structure and/or another copolymerizable reactant and/or a catalyst.

Briefly, the present invention features novel polymers containing imide groups, which comprise the copolymerizate, at a temperature ranging from 50° to 300° C., among:

(a) an N,N'-bis(maleimide) or a plurality of bis(maleimides) of the formula:

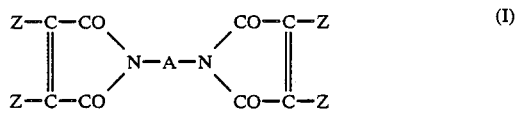

in which the symbols Z, which may be identical or different, are each H, CH$_3$ or Cl;

the symbol A is a divalent radical selected from among the following radicals cyclohexylenes; phenylenes, 4-methyl-1,3-phenylene; 2-methyl-1,3-phenylene; 5-methyl-1,3-phenylene; 2,5-diethyl-3-methyl-1,4-phenylene; or a radical of the formula:

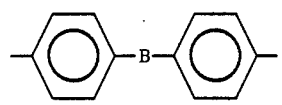

in which B is a single valence bond or a group or atom:

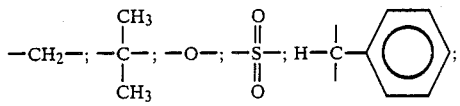

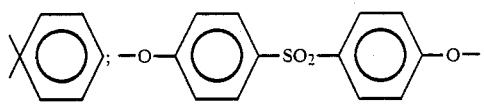

(b) at least one diamine containing a diorganopolysiloxane bridge corresponding essentially to the following general formula:

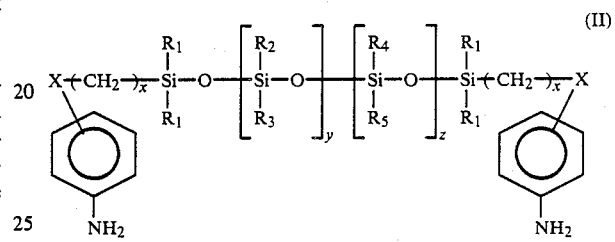

in which X, which is in the ortho, meta or para position with respect to the carbon atom of the benzene ring bonded to the nitrogen atom, is one of the following atoms or groups:

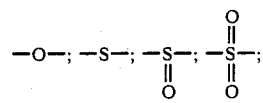

R$_1$, R$_2$, R$_3$, R$_4$ and R$_5$, which may be identical or different, are each a monovalent hydrocarbon radical selected from among: linear or branched chain alkyl radicals having from 1 to 12 carbon atoms, or substituted such radicals bearing one or more chlorine, bromine or fluorine atom substituents or a —CN group; a phenyl radical optionally substituted with one or more alkyl and/or alkoxy radicals having from 1 to 4 carbon atoms or with one or more chlorine atoms;

the symbol x is an integer ranging from 2 to 8;

the symbols y and z denote numbers, which may be identical or different, integral or fractional, the sum of which ranges from 0 to 100;

(c) optionally, at least one N,N'-bis(maleimide) containing a diorganopolysiloxane bridge corresponding essentially to the following general formula:

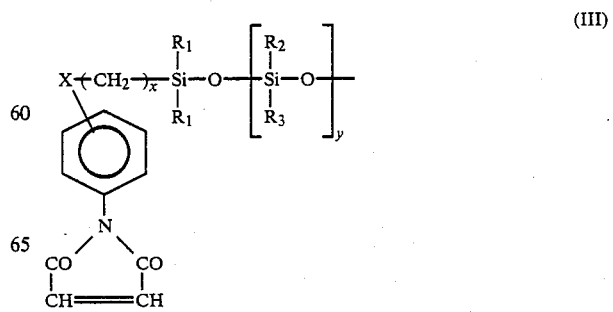

-continued

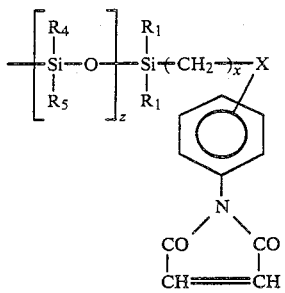

in which X, $R_1$, $R_2$, $R_3$, $R_4$, $R_5$, x, y and z are as defined above for the formula (II);

(d) optionally, one or more comonomers other than a bis(maleimide) of formula (I) or of formula (III) and containing one or more polymerizable carbon-carbon double bonds; and (e) optionally, a catalyst.

DETAILED DESCRIPTION OF THE PREFERRED EMBODIMENTS OF THE INVENTION

More particularly according to the present invention, exemplary of the bis(maleimides) of formula (I), especially representative are:

N,N'-(meta-phenylene)bis(maleimide),
N,N'-(para-phenylene)bis(maleimide),
N,N'-(4,4-diphenylmethane)bis(maleimide),
N,N'-(4,4-diphenyl ether)bis(maleimide),
N,N'-(4,4-diphenyl sulfone)bis(maleimide),
N,N'-(1,4-cyclohexylene)bis(maleimide),
N,N'-[4,4-(1,1-diphenylcyclohexane)]bis(maleimide),
N,N'-[4,4-(2,2-diphenylpropane)]bis(maleimide),
N,N'-(4,4-triphenylmethane)bis(maleimide),
N,N'-(2-methyl-1,3-phenylene)bis(maleimide),
N,N'-(4-methyl-1,3-phenylene)bis(maleimide),
N,N'-(5-methyl-1,3-phenylene)bis(maleimide).

These bis(maleimides) may be prepared according to the processes described in U.S. Pat. No. 3,018,290 and B.R. Pat. No. 1,137,290. Consistent herewith, N,N'-(4,4-diphenylmethane)bis(maleimide), either alone or mixed with N,N'-(2-methyl-1,3-phenylene)bis(maleimide), N,N'-(4-methyl-1,3-phenylene)bis(maleimide) and/or N,N'-(5-methyl-1,3-phenylene)bis(maleimide), are preferred.

With respect to the siloxane-diamines of formula (II) and the bis(maleimide)-siloxanes of the formula (III), when y and/or z are greater than 1, the compound in question is polymeric in structure and is rarely a single compound, but most often a mixture of compounds of the same chemical structure which differ in the number of repeated units in their molecule; this results in an average value of y and/or z which may be integral or fractional.

When the preparation of the polymers according to the invention is carried out, as set forth below, in an organic solvent or diluent, it is possible to use any one of the diamines of the formula (II) and, optionally, any one of the bis(maleimides) of formula (III).

Preferred diamines and optional bis(maleimides) are those of the formula (II) and, where appropriate, of the formula (III), in which:

(1) $X=-O-$; $R_1$, $R_2$, $R_3$, $R_4$ and $R_5$, which may be identical or different, are each a linear or branched chain alkyl radical having from 1 to 6 carbon atoms; $X = 2, 3, 4$ or 5; and $y+z$ ranges from 0 to 100, and preferably from 4 to 70;

(2) $X=-O-$; $R_1$, $R_2$ and $R_3$, which may be identical or different, are each a linear or branched chain alkyl radical having from 1 to 6 carbon atoms; $R_4$ and $R_5$ are each a phenyl radical; $x=2, 3, 4$ or 5; and $y+z$ ranges from 0 to 100, and preferably from 4 to 70;

(3) $X=-O-$; $R_1$, $R_2$ and $R_4$, which may be identical or different, are each a linear or branched chain alkyl radical having from 1 to 6 carbon atoms; $R_3$ and $R_5$ are each a phenyl radical; $x=2, 3, 4$ or 5; and $y+z$ ranges from 0 to 100, and preferably from 4 to 70;

(4) $X=-O-$; $R_1$ is a linear or branched chain alkyl radical having from 1 to 6 carbon atoms; $R_2$, $R_3$, $R_4$ and $R_5$ are each a phenyl radical; $x=2, 3, 4$ or 5; and $y+z$ ranges from 0 to 100, and preferably from 4 to 70.

Even more preferred diamines and optional bis(maleimides) are those of the formula (II) and, where appropriate, of the formula (III), in which:

(5) $X=-O-$, $R_1 = R_2 = R_3 = R_4 = R_5 =$ linear alkyl radicals having from 1 to 3 carbon atoms; $x=2, 3$ or 4; and $y+z$ ranges from 0 to 100, and preferably from 4 to 70;

(6) $X=-O-$; $R_1 = R_2 = R_3 =$ linear alkyl radicals having from 1 to 3 carbon atoms; $R_4 = R_5 =$ phenyl radical; $x=2, 3$ or 4; and $y+z$ ranges from 0 to 100, preferably from 4 to 70;

(7) $X=-O-$; $R_1 = R_2 = R_4 =$ linear alkyl radical having from 1 to 3 carbon atoms; $R_3 = R_5 =$ a phenyl radical; $x=2, 3$ or 4; and $y+z$ ranges from 0 to 100, preferably from 4 to 70;

(8) $X=-O-$; $R_1 =$ linear alkyl radical having from 1 to 3 carbon atoms; $R_2 = R_3 = R_4 = R_5 =$ phenyl radical; $x=2, 3$ or 4; and $y+z$ ranges from 0 to 100, preferably from 4 to 70.

Especially preferred diamines and optional bis(maleimides) are those of the formula (II) and, where appropriate, of the formula (III), in which:

(9) $X=-O-$; $R_1 = R_2 = R_3 = R_4 = R_5 =$ methyl radical; $x=3$; and $y+z$ ranges from 0 to 100, preferably from 4 to 70;

(10) $X=-O-$; $R_1 = R_2 = R_3 =$ methyl radical; $R_4 = R_5 =$ phenyl radical; $X=3$; and $y+z$ ranges from 0 to 100, preferably from 4 to 70;

(11) $X =-O-$; $R_1 = R_2 = R_4 =$ methyl radical; $R_3 = R_5 =$ phenyl radical; $X=3$; and $y+z$ ranges from 0 to 100, preferably from 4 to 70;

(12) $X=-O-$; $R_1 =$ methyl radical; $R_2 = R_3 = R_4 = R_5 =$ phenyl radical; $x=3$; and $y+z$ ranges from 0 to 100, preferably from 4 to 70.

As specific examples of the most preferred siloxane-diamines, the following are particularly representative:

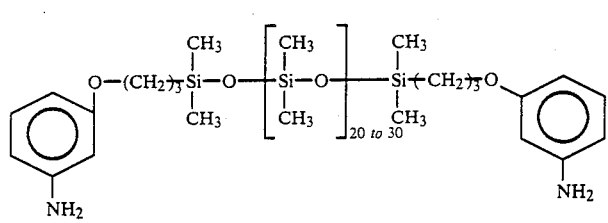
(13)
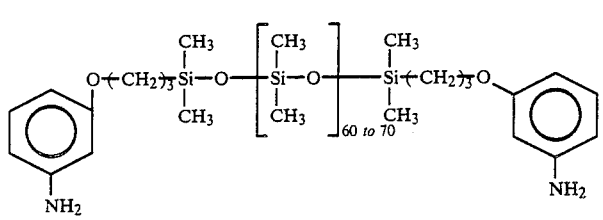
(14)
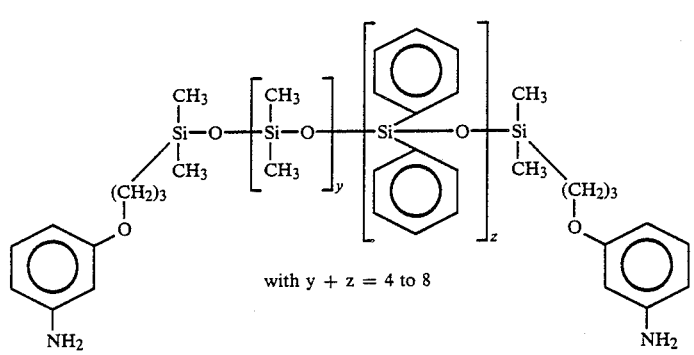
(15)
with y + z = 4 to 8
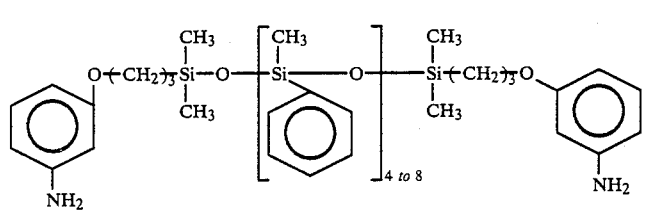
(16)
As specific examples of the most preferred optional bis(maleimide)-siloxanes, the following are particularly representative:
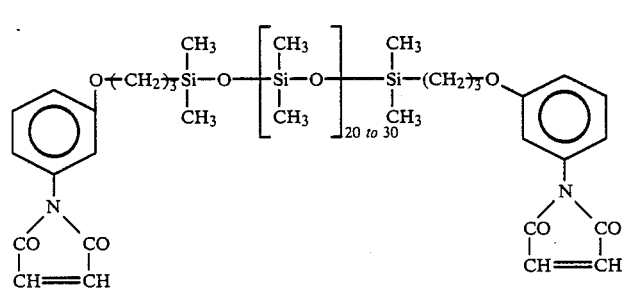
(17)

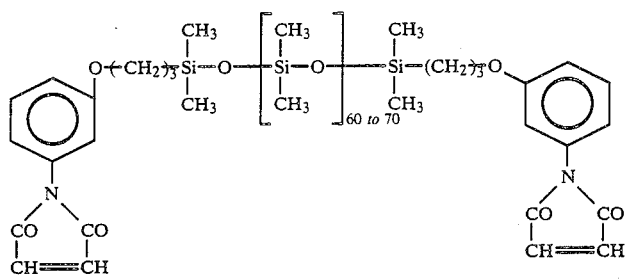
(18)

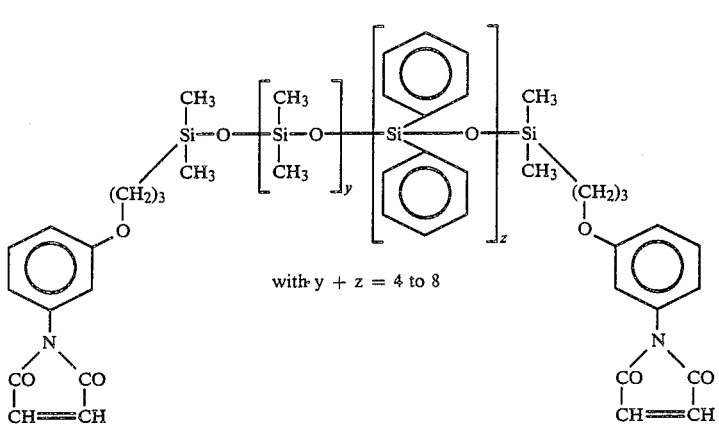
(19)

with y + z = 4 to 8

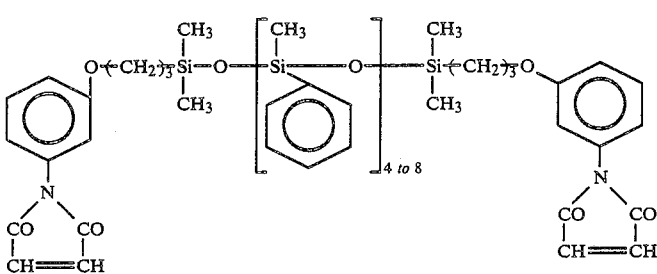
(20)

When the polymers according to the invention are prepared by bulk polymerization, it is preferable to use diamines of the formula (II) and optional bis(maleimides) of formula (III) in which the diorganopolysiloxane bridge contains a plurality of Si-phenyl or Si- (substituted phenyl) bonds. Suitable compounds of this type are those belonging to the following groups, classified in increasing order of preference:
Compounds Nos. 2, 3 and 4;
Compounds Nos. 6, 7 and 8;
Compounds Nos. 10, 11 and 12.

Among the diamines and the optional bis(maleimides) belonging to these preferred groups, those which are most especially suitable for the bulk preparation of the polymers are the compounds in which the ratio:

number of Si-phenyl (optionally substituted) bonds
—————————————————————————
number of Si-alkyl bonds is equal to at least 0.25. By way of specific examples of diamines and optional bis(maleimides) of this type, particularly representative are compounds Nos. 16 and 20.

The diamines of formula (II) containing a diorganopolysiloxane bridge are compounds which are known to the prior art. They are described, for example, in B.R. Pat. No. 1,062,418 and in U.S. Pat. No. 4,395,527.

According to these patents, a first method for preparing these diamines, which is especially applicable when a compound of the formula (II) in which y=z=0 can be obtained, that is to say, when a diamine containing a diorganodisiloxane group can be obtained, consists of reacting a compound of the formula:

in which X is as defined above and M is an alkali metal or alkaline earth metal, with a bis(haloalkyl)disiloxane of the formula:

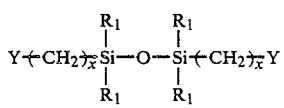

where x has the value indicated above and Y is a chlorine, bromine or iodine atom, and conducting the reaction at a temperature of from 20° to 200° C. in the presence of an aprotic polar solvent.

In the case where it is desired to prepare a diamine of formula (II) in which y and/or z are other than zero, a second described preparative technique consists of copolymerizing one mole of diamine containing a diorganopolysiloxane group, prepared as stated above, with a quantity of one or more cyclic diorganopolysiloxanes capable of providing y moles of siloxy groups of the formula:

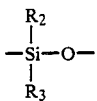

and/or z moles of siloxy groups of the formula:

In general, the reaction proceeds at a temperature of from 80° to 250° C. in the presence, in this instance also, of a solvent and optionally of a suitable catalyst.

Another technique for preparing the diamines of formula (II), with y and/or z being equal to zero or other than zero, comprises reacting an ethylenically unsaturated compound of the formula:

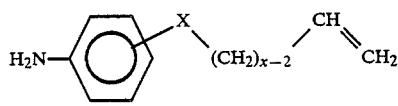

in which X, which is in the ortho, meta or para position with respect to the carbon atom of the benzene ring bonded to the nitrogen atom, and x are as defined above, with an alpha,omega-bis(hydrogeno)diorganopolysiloxane of the formula:

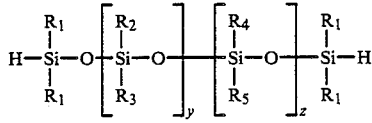

in which $R_1$, $R_2$, $R_3$, $R_4$, $R_5$, y and z are as defined above. This hydrosilylation reaction is carried out in bulk in the absence of solvent, and using a platinum-based catalyst. The alpha,omega-bis(hydrogeno)diorganopolysiloxanes employed are materials that are well known in the silicone industry, and in certain cases are commercially available. They are described, for example, in French Patents Nos. 2,486,952 and 2,058,988.

When it is determined to employ this hydrosilylation reaction for preparing a diamine of formula (II), the ethylenically unsaturated amino substrate which is very suitable for reaction with the alpha,omega-bis(hydrogeno)diorganopolysiloxane is, in particular, an allyloxyaniline of the formula:

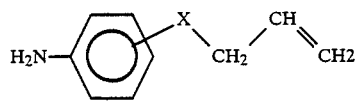

Under these favorable conditions, the compounds are hence diamines of formula (II) in which X=—O—, x=3 and $R_1$, $R_2$, $R_3$, $R_4$, $R_5$, y and z have the general or specific definitions given above.

As regards the optional bis(maleimide)-siloxanes of formula (III), these are novel compounds which are prepared by reacting the diamine of formula (II) with maleic anhydride in the presence of a dehydrating agent, a tertiary amine, an organic diluent and a catalyst.

The maleic anhydride is used in quantities at least equal to one mole per available $NH_2$ group; larger quantities are generally used, namely, on the order of 1.01 to 1.5 moles per available $NH_2$ group.

As the dehydrating agent, it is advantageous to use a lower carboxylic acid anhydride such as acetic anhydride, in quantities at least equal to one mole per available $NH_2$ group present in the molecule of diamine of formula (II) introduced. Larger quantities are generally used, namely, on the order to 1.05 to 1.5 moles per available $NH_2$ group.

Exemplary of the tertiary amines, particularly representative are trialkylamines as well as N,N-dialkylanilines in which the alkyl radicals have from 1 to 12 carbon atoms. Triethylamine and N,N-dimethylaniline are preferred. The quantities of tertiary amine generally range from 0.05 to 0.8 mole per available $NH_2$ group.

The reaction is carried out in a liquid organic diluent under the working conditions, in practice between 20 and 100 at atmospheric pressure. Exemplary such diluents, preferred are those which dissolve the starting maleic anhydride under the temperature conditions adopted for the reaction and in the presence of the other constituents of the reaction mixture.

Among these, the following are particularly representative:

(i) hydrocarbons such as benzene, toluene and cyclohexane, (ii) chlorinated derivatives such as chlorobenzene or methylene chloride, (iii) cyclic or acyclic ethers such as tetrahydrofuran, dioxane or ethyl ether, (iv) dialkyl ketones such as acetone or methyl ethyl ketone.

As catalysts, it is possible to use a nickel derivative which is soluble in the liquid phase of the reaction mixture, such as, for example, nickel salts of carboxylic acids, optionally hydrated, as well as the chelated forms of this metal. The acetate and acetylacetonate are especially suitable. These catalysts are employed in very small quantities, on the order of $0.5 \times 10^{-3}$ to $5 \times 10^{-3}$ moles per mole of available $NH_2$ group.

In practice, for carrying out the subject process, the first step is to react the maleic anhydride with the diamine of formula (II), in the selected diluent at a temperature ranging from 30° to 100° C. for a time ranging, according to the temperature, from a few minutes to 1 hour. The dehydrating agent, the tertiary amine and finally the catalyst are then added to the reaction medium, and the mixture is thereafter permitted to react under the temperature conditions previously adopted for a period ranging, according to the temperature, from 1 hour to 3 hours. In general, the reaction is terminated by adding a non-solvent such as water, and the product bis(maleimide) of formula (III) is then isolated according to the usual methods.

With respect to the polyimides obtained according to French Patent No. 1,555,564 by heating, in particular, N,N'-(4,4,'-diphenylmethane)bis(maleimide) and a diamine not containing a diorganopolysiloxane group, it has been found that the replacement of the diamine of the prior art by a siloxane-diamine of formula (II) enables cured polymers to be obtained having, in particularly flexural moduli which are markedly improved. The addition of an N,N'-bis(maleimide) containing a diorganopolysiloxane group of formula (III) to the polymerization medium containing the siloxane-diamine is a measure which enables, in addition, the resilience properties of the cured polymers to be markedly improved.

It may be advantageous in some cases to modify the polymers according to the present invention by employing a copolymerizable reactant (d). As an optional reactant (d) which is thus very suitable, the following may be mentioned in particular:

when it is desired, for example, to lower the fluidity of the polymerization medium:

($d_1$) either one or more monomers of the formula:

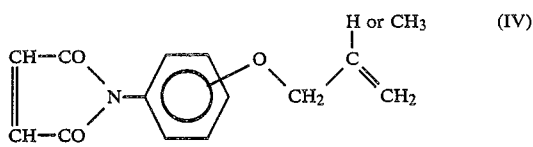

in which the allyloxy or methallyloxy radical is in the ortho, meta or para position with respect to the carbon atom of the benzene ring bonded to the nitrogen atom;

($d_2$) or a composition comprising: - a mixture of a monomer of the formula:

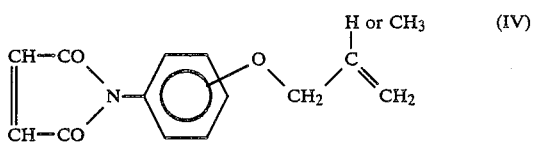

in which the allyloxy or methallyloxy radical is in the ortho, meta or para position with respect to the carbon atom of the benzene ring bonded to the nitrogen atom; - with:

at least one monosubstituted derivative of the formula:

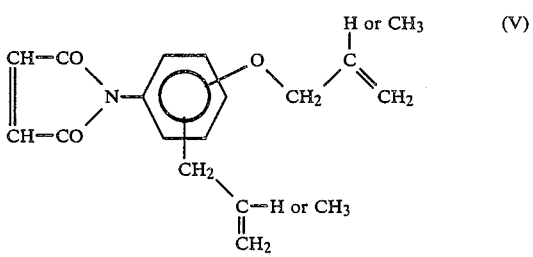

and optionally one or more disubstituted derivatives of the formula:

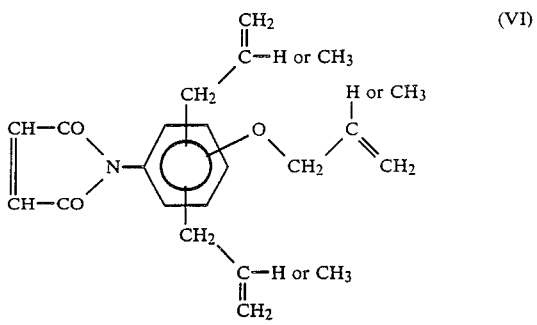

In the abovementioned composition serving as a reactant ($d_2$), the proportions of the various constituents of the mixture of the products of formulae (IV), (V) and optionally (VI) may vary over wide limits. In general, the proportions of the constituents are selected from within the following limits (expressing the percentage by weight of each of the constituents in the mixture):

at least 30%, and preferably from 50% to 80%, of N-(meth)allyloxyphenylmaleimide of formula (IV), from 5% to 50%, and preferably from 10% to 35%, of mono(meth)allyl substituted derivative(s) of formula (V), and from 0% to 20%, and preferably from 0% to 15%, of di(meth)allyl substituted derivative(s) of formula (VI), the sum of the constituents having in each case to be equal to 100% by weight.

when it is desired, for example, to improve further the flexural properties in the heated state:

($d_3$) one or more substituted heterocyclic compounds containing one or more carbon-carbon double bonds.

It should be clearly appreciated that mixtures of reactants ($d_1$)+($d_3$) or ($d_2$)+($d_3$) can be used as reactant (d).

As regards the optional reactant ($d_1$), this is advantageously selected from among:
N-(2-allyloxyphenyl)maleimide,
N-(3-allyloxyphenyl)maleimide,
N-(4-allyloxyphenyl)maleimide,
N-(2-methallyloxyphenyl)maleimide,
N-(3-methallyloxyphenyl)maleimide,
N-(4-methallyloxyphenyl)maleimide, and mixtures thereof.

The maleimides of formula (IV) are known compounds which are described in European Patent Application EP-A1-0,208,634.

As regards the optional reactant ($d_2$), the crude product obtained by carrying out the process defined below is preferably used as a compound comprising a mixture of N-(meth)allyloxyphenylmaleimide of formula (IV) with one or more (meth)allyl substitution derivatives of formula(e) (V) and optionally (VI).

This process is characterized in that it includes the following 3 stages, which are carried out sequentially in the same reactor:

the first stage comprises reacting an aminophenol in a solvent medium with maleic anhydride, at a temperature ranging from 20° C. to 200° C., for a period ranging, according to the temperature selected, from 30 minutes to 2 hours, and it provides a first reaction medium comprising an N-(hydroxyphenyl)maleamic acid;

the second stage comprises carrying out a (meth)allylation reaction of the abovementioned acid, by reacting the abovementioned first reaction medium with a (meth)allyl halide, at a pH which must be adjusted and maintained at a constant value between 7 and 14 by adding a specified quantity of an alkaline aqueous solution, and at a temperature ranging from 40° C. to 150° C., and it provides, after acidification and removal of the aqueous phase, to a second organic reaction medium comprising an N-[(meth)allyl oxyphenyl] maleamic acid, one or more N-[(meth)allyloxy, (meth)allylphenyl]maleamic acids and, where appropriate, one or more N-[(meth)allyloxy,di(meth)allylphenyl]maleamic acids;

the third stage comprises carrying out a cyclization reaction of the abovementioned maleamic acids, by reacting the abovementioned second reaction medium with a lower carboxylic acid anhydride in the presence of a tertiary amine and optionally a catalyst, and then in removing the reaction solvent, and it provides a crude reaction product which is a composition comprising a mixture composed of the following: at least 30% by weight, and preferably from 50% to 80%, of N-[(meth)allyloxyphenyl]maleimide, from 5% to 50% by weight, and preferably from 10% to 35% by weight, of one or more N-[(meth)allyloxy,(meth)allylphenyl]maleimides and from 0% to 20% by weight, and preferably from 0% to 15% by weight, of one or more N-[(meth)allyloxy,di(meth)allylphenyl]maleimides.

The 3 stages which have just been described are performed sequentially in a single solvent in order to enhance the simplicity of the process, but it is possible to perform a change of solvent during any stage without any disadvantage being incurred, the choice of solvent can be very wide, but since the second stage is carried out in a two-phase aqueous-organic medium, it may be desirable to employ a water-immiscible organic solvent, thereby considerably simplifying the treatment of the reaction mass. Among water-miscible or -immiscible solvents which are thus useful, preferred are those which dissolve the starting aminophenol under the temperature conditions adopted for the synthesis. Among these solvents, there may be mentioned, for example: alcohols (for example methanol, ethanol, butanol); ketones (for example acetone, methyl ethyl ketone, methyl isobutyl ketone); nitriles (for example benzonitrile, propionitrile, acetonitrile); esters (for example ethyl or butyl acetate); aromatic solvents (for example anisole, chlorobenzene); and halogenated hydrocarbons (for example chloroform, dichloromethane, dichloroethane).

As regards the first stage of the process, it may be pointed out that the concentration of the starting reactants in the solvent is not critical. Nevertheless, no advantage is gained either by diluting the reactants excessively, in the interest of productivity, or by concentrating them excessively, in order that the mixture shall be readily stirrable. In this first stage, the maleic anhydride is used in quantities at least equal to one mole per mole of aminophenol; larger quantities, namely, one the order of 1.01 to 1.5 moles per mole of aminophenol, are generally used. In addition, the temperature preferably ranges from 40° C. to 60° C.

As regards the second stage, this is initiated by adding to the reaction medium the quantity of an alkaline aqueous solution, for example an aqueous NaOH solution, required on the one hand for salifying the N-(hydroxyphenyl)maleamic acid, and on the other hand for obtaining the desired pH. The pH will be maintained constant throughout the reaction by adding sodium hydroxide; preferably, the pH is adjusted and maintained at a constant value from 10 to 12. The allylation reaction is preferably carried out with (meth)allyl bromide or chloride. The quantity of (meth)allyl halide is on the order of 1.5 to 10 moles per moles of phenolic OH group, and preferably on the order of 2 to 4. The excess of this reactant can be recovered upon completion of the operation and recycled in a following operation. The time used for adding the (meth)allyl halide is not critical, and it can range from 1 hour to 5 hours, and preferably from 2 hours to 4 hours. In this second stage, the temperature preferably ranges from 60° C. to 100° C. It will be appreciated that, at the end of the stage, the aqueous phase is acidified to a pH approximately equal to 1 with usual acids, preferably inorganic hydracids or oxyacids. The aqueous layer is removed and the organic layer is retained in the reactor.

As regards the third stage of the process, acetic anhydride, in quantities at least equal to one mole per mole of HOOC—CH=CH—CO—NH— group to be cyclized, is advantageously used as a lower carboxylic acid anhydride. Larger quantities, namely, on the order of 1.05 to 1.5 moles per maleamic group, are generally used.

Among suitable tertiary amines, there may be mentioned, in particular, trialkylamines as well as N,N-dialkylanilines in which the alkyl radicals have from 1 to 12 carbon atoms. Triethylamine and N,N-dimethylaniline are preferred. The quantities of tertiary amine range from 0.05 to 2 moles per mole of HOOC—CH=CH—CO—NH— group.

As catalysts, it is possible to use, for example, nickel salts of carboxylic acids, optionally hydrated, as well as the chelated forms of this metal. The acetate and acetylacetonate are especially suitable. These catalysts are employed in very small quantities, on the order of 0.05 to 1.5 g per mole of HOOC—CH=CH—CO—NH— group, and preferably on the order of 0.1 to 0.8 g.

In this third stage, the temperature is not critical and only influences the kinetics of the reaction. This temperature may range, for example, from 40° C. to 150° C., and preferably ranges from 60° C. to 80° C. At the end of this stage, the solvent is removed by vacuum distillation and the crude reaction product, having the appearance of an oil, is obtained.

In a very preferred embodiment of the present invention, the aforementioned process is readily applied, starting with meta-aminophenol, to the preparation of compositions comprising mixtures based on: N-[3-(meth)allyloxyphenyl]maleimide + N-[3-(meth)allyloxy-4-(meth)allyloxyphenol]maleimide + N-[3-(meth)allyloxy-6-(meth)allyloxyphenyl]maleimide +, where appropriate, N-[3-(meth)- allyloxy-4,6-di(meth)allylphenyl]maleimide.

It will be appreciated that, starting with orthoaminophenol, compositions are produced comprising mixtures based on: N-[2-(meth)allyloxyphenyl]maleimide + N-[2-(meth)- allyloxy-3-(meth)allylphenyl]maleimide + N-[2-(meth)allyloxy5-(meth)allylphenyl]maleimide +, where appropriate, N-[2- (meth)allyloxy-3,5-di(meth)allylphenyl]maleimide. It should be noted that, starting with para-aminophenol, compositions are produced comprising mixtures based on: N-[4-(meth)allyloxyphenyl]maleimide + N-[4-(meth)allyloxy-3-[4-(meth)allyloxyphenyl]maleimide + N-[4-(meth)allyloxy-3-(meth)allylphenyl]maleimide +, where appropriate, N-[4-(meth)allyloxy 3,5-di(meth)allylphenyl]maleimide.

As regards the optional reactant $(d_3)$, this is advantageously selected from among the vinylpyridines, N- vinylpyrrolidone, allyl isocyanurate, triallyl isocyanuate and vinyltetrahydrofuran.

The reactivity of the constituents (a), (b) and, where appropriate, (c) and/or (d) of the polymerization medium according to the invention may be increased, for example when the applications envisaged require operations to be carried out on an injection molding machine, by adding a catalyst (e) which can be either (e₁) a free-radical polymerization initiator such as, for example, dicumyl peroxide, lauroyl peroxide or azobisisobutyronitrile, or (e₂) an imidazole compound.

The said imidazole compound (e₂) has the general formula:

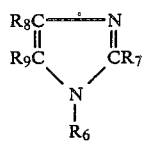
(VII)

in which $R_6$, $R_7$, $R_8$ and $R_9$, which may be identical or different, are each a hydrogen atom, an alkyl or alkoxy radical having from 1 to 20 carbon atoms, or a vinyl, phenyl or nitro radical, with the proviso that $R_8$ and $R_9$ may together form, with the carbon atoms from which they depend, a single ring such as, for example, a benzene ring, with the further proviso that $R_6$ may be carbonyl group bound to a second imidazole ring.

As specific examples of imidazole compounds (e₂), representative are, in particular: imidazole or glyoxaline, 1-methylimidazole, 2-vinylimidazole, 1,2-dimethylimidazole, 1-vinylimidazole, 1-vinyl-2-methylimidazole, benzimidazole and carbonyldiimidazole.

In the heat-resistant polymers defined above, the quantities of reactants (a) and (b) are selected such as to have, by weight with respect to the total weight of these constituents:

from 50 to 98%, and preferably from 70 to 95%, of bis(maleimides) (s) (a) of formula (I), and from 2 to 50%, and preferably from 5 to 30%, of siloxane-diamine (b) of formula (II).

As regards the quantity of the optional bis(maleimide)siloxane (c) of formula (III), this generally represents less than 40%, and preferably from 5 to 30%, of the total weight of the reactants (a) + (b). Still more preferably, this quantity represents from 10 to 20% of the total weight of the reactants (a) + (b).

As regards the quantity of the optional reactant (d), this generally represents less than 60%, and preferably from 5% to 50%, of the total weight of the reactants (a) + (b).

As regards the optional catalyst (e), according to its nature and according to the rate of polymerization desired at the stage when the reaction is carried out, it is employed at a level ranging from 0.01 to 1% by weight with respect to the combination of the reactants (a) + (b) +, optionally, (c) and/or (d), and preferably within the range from 0.05 to 0.5%.

The polymers according to the invention may be prepared by directly heating the reactant (a), the reactant (b) and, optionally, the reactants (c) and/or (d) with, if required, the catalyst (e), at least until a homogeneous liquid mixture is obtained. The temperature may vary according to the physical state of the compounds present, but generally ranges from 50° C. to 300° C. It is advantageous to bring the starting compounds to, and maintain them in, a stage of intimate mixture before and during the heating, for example using efficient stirring. When the compound (e) is employed, the latter is preferably added at the beginning to the well stirred reaction mixture containing the reactants. When this compound is particularly active, in order to avoid its encapsulation in the polymer network formed, it is desirable to add it in a solvent or diluent which is compatible with the reaction medium; it was found that it could be advantageous to use as solvent or diluent either the reactant (b), or the reactant (c) when one is used, or alternatively one of the polar organic liquids referred to below.

The preparation of the polymers according to the invention may also be accomplished by heating the mixture of reactants in an organic diluent which is liquid over at least part of the range 50° C. -250° C. Among these diluents, representative are, in particular, aromatic hydrocarbons such as xylenes and toluene, halogenated hydrocarbons such as chlorobenzenes, polar solvents such as dioxane, tetrahydrofuran and dibutyl ether, dimethylformamide, dimethyl sulfoxide, N-methylpyrrolidone, dimethylacetamide, methyl glycol, cyclohexanone and methyl ethyl ketone. The solutions or suspensions of polymers may be employed as they are for many applications; it is also possible to isolate the polymers, for example by filtration, where appropriate after precipitation by means of an organic diluent which is miscible with the solvent employed. In this context, it is advantageously envisaged to use a hydrocarbon whose boiling point does not substantially exceed 120° C.

It will be appreciated that the properties of the polymers according to the invention may vary widely, depending in particular on the exact nature of the reactants introduced, the selected proportions of reactants and the precise conditions of temperature adopted within the range stated above. As regards the polymers obtained, the latter may be cured polymers which are insoluble in the usual solvents such as, for example, the compounds mentioned in the preceding paragraph, and which do not display significant softening below the temperature at which they begin to decompose.

However, these polymers can also take the form of prepolymers (P) which are soluble in polar organic solvents and possess a softening point at a temperature below 200° C. (in general this softening point ranges from 50° to 150° C.). These prepolymers may be obtained in bulk by heating the mixture of reactants until a homogeneous or pasty product is obtained, at a temperature generally ranging from 50 to 180° C., for a period of time which can range from a few minutes to a few hours, this period becoming shorter as the temperature adopted is raised. Before the mixture of reactants is subjected to heating, it is advantageous, in this case also, to mix its constituents intimately beforehand by stirring. In this case also, there is a preferred method for introducing the compound (e), this being the method described above in relation to the direct preparation of cured polymers. The preparation of the prepolymers may also be performed in suspension of in solution in a diluent which is liquid over at least part of the range 50° -180° C.

In cases where it is determined to employ the optional reactants (c) and/or (d), it should be noted that these prepolymers (P) can also be obtained by forming, from the reactant (a) and the reactant (b), a prepolymer (PP) which is then reacted with the reactants (c) and/or (d) and, if required, the compound (e). It is also possible to first prepare a prepolymer (P'P') by heating the mixture of reactant (b), reactants (c) and/or (d) and, if required, compound (e), and then reacting it with the reactant (a) to obtain the prepolymer (P). The conditions of temperature and time used for the preparation of the prepolymers (PP) of (P'P') and for their conversion to prepolymers (P) are those described above in relation to the preparation of the prepolymers (P) by directly mixing the reactants (a), (b) and, optionally, (c) and/or (d) with, if required, the compound (e).

The prepolymers (P) may be used in the bulk liquid state, simple hot casting sufficing for shaping and producing molded articles. It is also possible, after cooling and grinding, to use them in the form of powders which are exceptionally suitable for compression molding operations, optionally in the presence of fillers in the state of powders, spheres, granules, fibers or flakes. In the form of suspensions or solutions, the prepolymers (P) may be used for producing coatings and preimpregnated intermediate articles whose reinforcement may consist of fibrous materials based on aluminum silicate or oxide or zirconium silicate or oxide, carbon, graphite, boron, asbestos or glass. It is also possible to use these prepolymers (P) for producing cellular materials after the incorporation of a blowing agent such as, for example, azodicarbonamide.

In a second stage, the prepolymers (P) may be cured by heating to temperatures on the order of 300° C., generally between 150° and 300° C.; an additional shaping may be performed during the curing, optionally under vacuum or under a pressure above atmospheric pressure, it also being possible for these operations to be consecutive.

In cases where it is determined to employ the optional reactants (c) and/or (d), it is within the ambit of the invention if polymers according to the invention, which are not in the form of prepolymers (P), are prepared using an intimate mixture of prepolymer (PP), reactants (c) and/or (d) and, if required, compound (e), or an intimate mixture of prepolymer (P'P') and reactant (a), which is heated in bulk under the conditions described above.

The polymers according to the invention are of value in industrial fields requiring materials endowed with good mechanical and electrical properties as well as great chemical inertness at temperatures of 200° to 300° C. By way of examples, they are suitable for the manufacture of insulators in plate or tubular form for electrical transformers, printed circuit bases, pinions, rings, and the like. The preimpregnated articles are usable for the production of parts having a variety of shapes and functions in many industries such as, for example, in the aeronautical industry. These parts, referred to as laminates, which may be bodies produced by rotation, are obtained by depositing several layers of prepregs on a form or support. The prepregs can also be used as reinforcements or as a means of repairing damaged parts. It is also possible to contrive parts according to filament winding techniques, with or without a support; it is possible, as well, to carry out injection molding or pultrusion. It will be recalled that, in order to make, for example, molded articles, it is possible to use either the mixture of the reactants or a prepolymer (P) as the starting material. When the mixture of the reactants is used directly as the starting material, this mixture is given the shape of the desired article and the curing is then performed by heating. When the prepolymer (P) is used as the starting material, it may be molded by simple hot casting or by injection, and its curing is then induced by heating.

In order to further illustrate the present invention and the advantages thereof, the following specific examples are given, it being understood that same are intended only as illustrative and in nowise limitative.

EXAMPLE 1

1. Example according to the present invention:

One half of the total charge of N,N'-(4,4'-diphenylmethane)bis(maleimide) was introduced over the course of 5 minutes into a glass reactor equipped with an anchor type stirrer and a side tube enabling volatile products to escape and preheated to 160° C. by means of a suitable oil bath. This total charge represented 48.15 g (0.134 mole). 10.7 g (0.011 mole) of the diamine containing a diorganopolysiloxane bridge, which is described in section 2 below, were then added, and the temperature was then raised to 180° C. The remainder of the N,N'-(4,4'-diphenylmethane)bis(maleimide) (24.075 g) was then added over the course of 4 minutes under stirring. The reactants were permitted to react under these conditions for 12 minutes, and a reduced pressure of $13 \times 10^2$ Pa was then applied for an additional 3 minutes.

The reaction mixture, which was a clear liquid mass red in color, was then poured into a mold preheated to 200° C., for the purpose of preparing plates having the dimensions $140 \times 100 \times 4$ mm, which were subjected to the following curing cycle:

20 hours at 200° C.

2 hours from 200° C. to 25° C.

After release from the mold, the plates based on cured polymer were cut in order to obtain test pieces:

having the dimensions $30 \times 7 \times 4$ mm, on which the flexural breaking strength (Sf) and the flexural modulus (Mf) were measured (Young's modulus: INSTRON apparatus with gap of 25.4 mm between supports);

having the dimensions $50 \times 10 \times 4$ mm, on which the glass transition temperature (Tg) was measured by DMA (Dynamic Mechanical Analysis). The Tg values were determined from the curves for flexural modulus as a function of temperature, obtained by dynamic mechanical analysis carried out on an apparatus referred to as DMA 983 marketed by DUPONT. The temperature range explored extended from 25° C. to 400° C., with a rate of temperature increase of 3° C. per minute under an inert atmosphere. The resonance frequency was 20 Hz. The data were collected and processed by the apparatus referred to as a DUPONT 1090 Analyzer.

By way of a comparative example, the operations described above were repeated, but using the following reactants: N,N'-(4,4'-diphenylmethane)bis(maleimide) and 4,4'-diaminodiphenylmethane in proportions by weight [82% by weight of bis(maleimide) and 18% by weight of diamine]corresponding to those of Example 1. These reactants were introduced into the reactor preheated to 160° C. The mixture was then degassed for 1 minute and thereafter permitted to react at 160° C. for 9 minutes.

The values of the mechanical properties are reported in the following table:

TABLE

| | Initial Sf in MPa at 25° C. | Initial Mf in MPa at 25° C. | Tg in °C. |
|---|---|---|---|
| Example 1 | 100 | 5100 | 275 |
| Comparative | 226 | 3400 | 300 |

TABLE-continued

| | Initial Sf in MPa at 25° C. | Initial Mf in MPa at 25° C. | Tg in °C. |
|---|---|---|---|
| Example | | | |

2. Process for preparing the diamine containing a diorganopolysiloxane group used in Example 1:

This siloxane-diamine had the following formula:

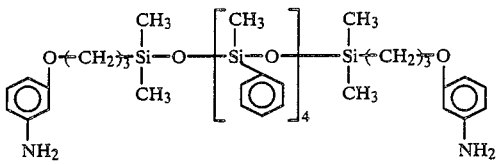

A glass reactor equipped with a central stirrer, a dropping funnel and a reflux condenser, in which a slight overpressure of dry nitrogen was established, was charged with 312 g (0.46 mole) of an alpha,omega-bis(-hydrogeno)diorganopolysiloxane of formula:

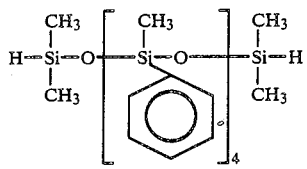

having a molecular weight on the order of 67 g.

The reactor was then placed in an oil bath preheated to 55° C., after which the catalyst was added. The latter was the Karsted catalyst (complex based on elementary platinum and 1,3-divinyl-1,1,3,3-tetramethyldisiloxane ligands): it was dissolved in toluene (concentration 3.5% by weight) and 1.49 cm$^3$ of this catalyst solution were introduced with a syringe; the ratio r (weight of elementary platinum introduced/weight of the reaction mass) was equal to $91 \times 10^{31\ 6}$ 137 g (0.092 mole) of meta-allyloxyaniline were then permitted to flow gradually into the reactor over a period of 60 minutes, in order to control the exothermicity of the reaction. Thirty minutes after the addition was complete, the mixture was returned to room temperature. The product obtained, weighing 448.9 g, was a clear viscous oil, orange-brown in color, possessing a proton NMR spectrum in agreement with the structure of the diamine given above.

Its weight was on the order of 976 g. Under these conditions, the degree of conversion of the reactants introduced was 100% (neither amine nor hydrogenated siloxane oligomer was detected by NMR and infrared analysis), and the yield by weight of desired diamine was 100%.

EXAMPLE 2

This example is also according to the invention.

0.1 g of imidazole, dissolved in 20 g (0.020 mole) of the diamine containing a diorganopolysiloxane bridge which was described above in section 2 of Example 1, was introduced at 160° C., over the course of 2 minutes and under stirring, into the reactor used in Example 1. 80 g (0.233 mole) of N,N'-(4,4-diphenylmethane)bis(-maleimide) were then charged over the course of 5 minutes, after which the reaction mass was permitted to react for 13 minutes under stirring. At the end of this time, the reaction mass was cooled and subjected to grinding.

The prepolymer thereby obtained in powder form possessed the following properties: softening point: 100° C.; soluble in cyclohexanone to the extent of 45% by weight of dry extract; the gel time at 150° C. of the collodion-like product containing 45% by weight of the prepolymer in cyclohexanone was 38 minutes (the gel time was measured using a SUNSHINE apparatus; the zero time was defined by the instant of immersion of the tube containing the collodion-like product in a thermostatic bath at the temperature of measurement).

With this prepolymer a collodion-like product was prepared containing 45% by weight of prepolymer in cyclohexanone. This collodion-like product was used for coating a glass fabric manufactured by the company PORCHER under reference 7628, the basis weight of which was 200 g/m$^2$ and which had been subjected to a treatment with UNION CARBIDE a 1100 gamma-aminopropyltriethoxysilane. The impregnated fabric was dried in a ventilated atmosphere at 160° C. for 12 minutes. 6 rectangles (145 × 100 mm) were then cut and stacked with two pieces of copper foil 35 micrometers thick placed on the outer two face surfaces of the stack, and the assembly was placed between the plates of a press under the following conditions: heating 15 minutes at 160° C., followed by 1 hour 15 minutes at 180° C. under $40 \times 10^5$ Pa; and 16 hours at 200° C. under atmospheric pressure.

The adhesion of the copper to the 6-ply laminate prepared was examined: this adhesion, measured with an INSTRON dynamometer by pulling the copper at an angle of 90° C. (according to standard MIL P 55 617 B with a rate of pull of 55 mm/min) was on the order of 12.7 N/cm.

EXAMPLE 3

1. This example is also according to the invention:

A mixture of 10 g (0.0088 mole) of the bis(maleimide) containing a diorganopolysiloxane bridge which is described in section 2 below and 0.1 g of imidazole was introduced into the reactor used in Example 1, preheated to 160° C. This introduction was carried out over the course of 2 minutes under slow stirring. After the reactor had been removed from the hot oil bath used as a means of heating, 10 g (0.010 mole) of the diamine containing a diorganopolysiloxane bridge which was described above in section 2 of Example 1 were then added over the course of 2 minutes. The reactor was replaced in the oil bath thermostated at 160° C., and 80 g (0.223 mole) of N,N'-(4,4'-diphenylmethane)bis(maleimide) were added over the course of 5 minutes under stirring. The reactants were permitted to react for an additional 9 minutes under stirring (the medium was homogeneous after 5 minutes) and a reduced pressure of $10 \times 10^2$ Pa was applied for 2 minutes.

The reaction mass was then poured into a mold preheated to 150° C., for the purpose of preparing plates having the dimensions 140 × 100 × 4˙mm, which were subjected to the following curing cycle:

1 hour 40 minutes from 150° C. to 25° C., 16 hours at 250 C., and 2 hours at between 25° C. and 25° C.

After release from the mold, the plates based on cured polymer were cut in order to obtain test pieces:

having the dimensions 30 × 7 × 4 mm, on which the Sf and Mf values were measured as described above in Example 1;

having the dimension's 60 × 10 × 4 mm, on which unnotched CHARPY impact tests at 25° C. were carried out for measuring the resilience (Rc) (according to standard NF T 51035).

The values for the mechanical properties were as follows:

| Results for flexural properties: | |
|---|---|
| at 25° C.: | initial Sf = 100 MPa |
| | initial Mf = 1830 MPa |
| at 250° C.: | initial Sf = 52 MPa |
| | initial MF = 1500 MPa |
| Resilience: | |
| at 25° C.: | Rc = 10.3 kj/m² |

2. Process for preparing the bis(maleimide) containing a diorganopolysiloxane bridge used in Example 3:

This bismaleimide had the following formula:

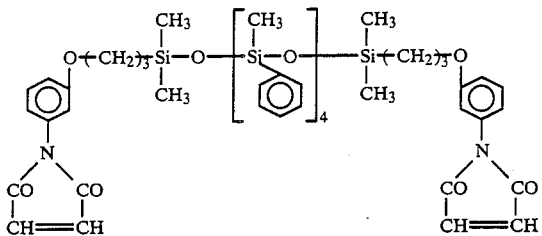

The following materials were introduced simultaneously over the course of 10 minutes, using two dropping funnels, into a glass reactor equipped with a central stirrer and a reflux condenser, in which a slight overpressure of dry nitrogen was established and which was placed in an oil bath preheated to 55° C.: 20 cm³ of a solution in acetone of 25 g (0.025 mole and 0.02 NH₂ group) of the siloxane-diamine prepared above in section 2 of Example 1, and 15 cm³ of a solution in acetone of 6.4 g (0.055 mole) of maleic anhydride.

When the additions were complete, each funnel was rinsed with 5 cm³ of acetone, which were then added to the reaction mass maintained under stirring for 15 minutes.

The dropping funnel which contained maleic anhydride was charged with 6.1 g (0.06 mole) of acetic anhydride, and the other funnel was charged with 1.67 g (0.0165 mole) of triethylamine.

These two compounds were then permitted to flow into the reactor, after which 0.3 cm³ of an aqueous solution containing 0.0528 mole of nickel acetate for 100 cm³ of solution was added.

The reaction mixture was maintained under reflux and stirring for 2 hours, 30 minutes. The temperature was then lowered to 20° C.

The reaction mixture was diluted with 80 cm³ of ice-cold water (5° C.) under vigorous stirring, and the oily product present was then extracted with 80 cm³ of ethyl acetate. The organic phase obtained was washed three times with 80 cm³ of water such that a pH of 6 was obtained in the washing water, and then dried for 2 hours over anhydrous sodium sulfate. After filtration, the ethyl acetate was removed from the organic phase by evaporation, completing this operation under reduced pressure (approximately 70 Pa) at 60° C., and 27.3 g (equivalent to a yield of 96% by weight with respect to the theoretical value) of an orange-brown viscous product was collected, the NMR spectrum of which was in agreement with the structure of the desired bis(maleimide) defined above. Its weight was on the order of 1136 g. In proton NMR (solvent: CDCl₃; reference: tetramethylsilane), the absence of the starting diamine was noted and the following chemical shifts, expressed in ppm, were noted:

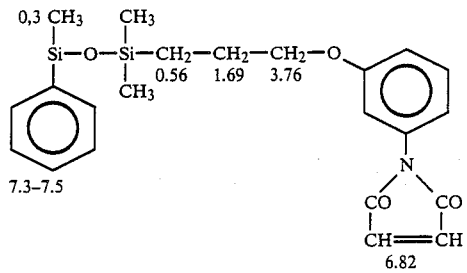

the ratio: $\dfrac{\text{number of Si-phenyl bonds}}{\text{number of Si-methyl bonds}}$ were found to be equal to 0.5.

In infrared spectrometry, the presence of the following bands was noted: ν (imide C=O) = 1710 - 1730 cm⁻¹; ν (maleimide C—N—C) = 1160 cm⁻¹; ν (C—N—C) = 1400 cm⁻¹.

EXAMPLE 4

This example is also according to the invention.

A mixture consisting of the following reagents was introduced into the reactor used in Example 1, preheated to 160° C.:

(i) 20 g (0.087 mole) of N-(3-allyloxyphenyl)maleimide, (ii) 12 g (0.0106 mole) of the bis(maleimide) containing a diorganopolysiloxane bridge which was described in section 2 of Example 3, and (iii) 0.1 g of imidazole (this was in the state of dissolution in the mixture). This introduction was carried out over the course of 2 minutes under slow stirring.

After the reactor had been removed from the oil bath used as heating device, 6 g (0.006 mole) of the diamine containing a diorganopolysiloxane bridge which was described above in section 2 of Example 1 was then added over the course of 4 minutes. The reactor was immersed again in the oil bath thermostated at 160° C., and 62 g (0.173 mole) of N,N'-(4,4'-diphenylmethane)-bis(maleimide) were added over the course of 4 minutes under stirring. The reactants were permitted to react for an additional 9 minutes under stirring (the medium became homogeneous after 5 minutes) and a reduced pressure of 10 × 10² Pa was applied for 2 minutes.

The reaction mass was then molded, cured and tested as described above in Example 3.

The values for the mechanical properties were as follows:
Results for flexural properties:
  at 25° C.: initial Sf = 100 MPa
    Sf after 1000 hours at 250° C. = 83 MPa
    initial Mf = 2120 MPa
    Mf after 1000 hours at 250 C. = 2600 MPa
  at 250° C.: initial Sf = 58 MPa
    Sf after 1000 hours at 250° C. = 35 MPa
    initial Mf = 1700 MPa Mf after 1000 hours at 250° C. = 1900 MPa
Resilience:
  at 25° C.: Rc = 13.1 kj/M²
Results in DMA:
  Tg = 280° C.

Excellent preservation of the modulus as a function of temperature up to 350° C. was also observed (50% retention).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A heat-resistant maleimido polymer comprising the copolymerizate of:
   (a) at least one N,N,-bis (maleimide) of the formula:

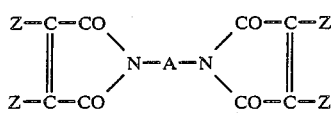

(I)

in which the symbols Z, which may be identical or different, are each H, CH₃ or Cl;

the symbol A is a cyclohexylene; phenylene; 4-methyl-1,3-phenylene; 2-methyl-1,3-phenylene; 5-methyl-1,3-phenylene; 2,5-diethyl-3-methyl-1,4-phenylene; or a radical of the formula:

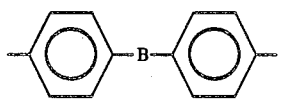

in which B is a single valence bond or a group or atom selected from

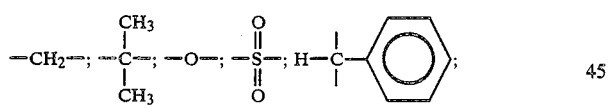

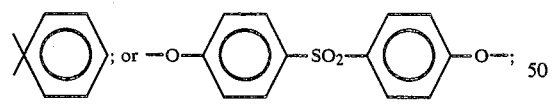

(b) at least one diamine containing a diorganopolysiloxane bridge and having the following general formula:

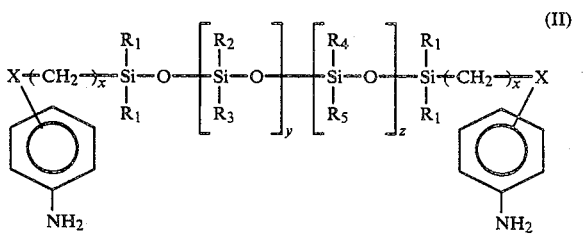

(II)

in which X, which is in the ortho, meta or para position with respect to the carbon atom of the benzene ring bonded to the nitrogen atom, is one of the following atoms or groups:

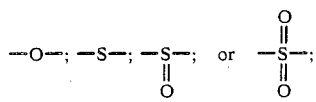

$R_1$, $R_2$, $R_3$, $R_4$ and $R_5$, which may be identical or different, are each a linear or branched chain alkyl radical having from 1 to 12 carbon atoms, or a substituted such radical bearing one or more chlorine, bromine or fluorine atom substituents or a —CN group; or a phenyl radical optionally substituted with one or more alkyl and/or alkoxy radicals having from 1 to 4 carbon atoms or with one or more chlorine atoms;

the symbol x ranging from 1 to 8; and the symbols y and z denote numbers, which may be identical or different, integral or fractional, the sum of which ranges from 0 to 100;

(c) optionally, at least one N, N'-bis(maleimide) containing a diorganopolysiloxane bridge and having the following general formula:

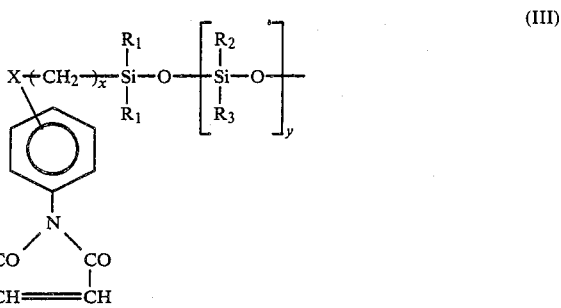

(III)

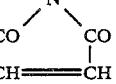

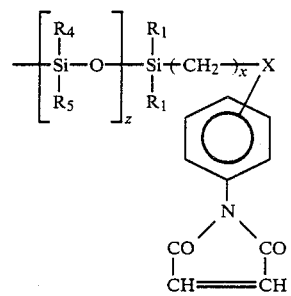

in which X, $R_1$, $R_2$, $R_3$, $R_4$, $R_5$, x, y and z are as defined above;

(d) optionally, at least one comonomer other than a bis (maleimide) of formula (I) or formula (III) and containing one or more copolymerizable carbon-carbon double bonds; and (e) optionally, a catalyst selected from a free-radical polymerization initiator or an imidazole compound.

2. The heat-resistant polymer as defined by claim 1, comprising at least one of the following catalysts (e):
   (e₁) a free-radical polymerization initiator; or
   (e₂) an imidazole compound of the formula:

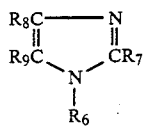

in which $R_7$ is a hydrogen atom, an alkyl or alkoxy radical having from 1 to 20 carbon atoms, or a vinyl, phenyl or nitro radical, $R_8$ and $R_9$ are the same or different and are each selected from the same radicals as $R_7$ or $R_8$ and $R_9$ together form, with the carbon atoms from which they depend, a single ring member, and $R_6$ is selected from the same radicals as $R_7$ or is a carbonyl group bonded to a second imidazole ring.

3. The heat-resistant polymer as defined by claim 1, comprising from 50 to 98% by weight of the bis(maleimide) (s) (a) of formula (I), and from 2 to 50% by weight of the siloxanediamine (b) of the formula (II).

4. The heat-resistant polymer as defined by claim 1 comprising from 5 to 30% by weight of bis(maleimide)-siloxane (c) of formula (III), based on the total weight of the reactants (a) + (b).

5. The heat-resistant polymer as defined by claim 1, comprising from 5 to 50 % by weight of comonomer (d), based on the total weight of the reactants (a) + (b).

6. The heat-resistant polymer as defined by claim 2, comprising from 0.01 to 1 % by weight of said catalyst (e), based on the total weight of the constituents (a) + (b) + optionally, (c) and/or (d).

7. The heat-resistant polymer as defined by claim 1, in cured state, solvent insoluble, and exhibiting essentially no softening below its decomposition temperature.

8. The heat-resistant thermosettable prepolymer comprising the copolymerizates defined in claim 1, soluble in polar organic solvents and having a softening point at a temperature below 200° C.

9. A shaped article comprising the heat-resistant polymer as define by claim 1.

10. A shaped article comprising the heat-resistant polymer as defined by claim 7.

11. A shaped article comprising the heat-resistant polymer as defined by claim 8.

12. The heat-resistant polymer as defined by claim 1, in which (d) is:

(d₁) at least one comonomer of the formula:

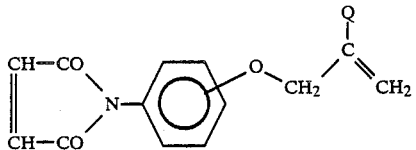

in which the allyloxy or methallyloxy radical is in the ortho, meta or para position with respect to the carbon atom of the benzene ring bonded to the nitrogen atom; or (d₂) a composition comprising a mixture of:

(i) at least one monomer of the formula:

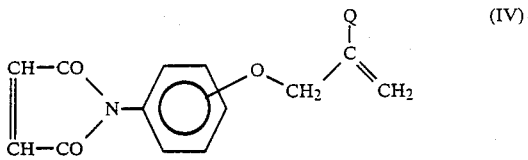

in which the allyloxy or methallyloxy radical is in the ortho, meta or para position with respect to the carbon atom of the benzene ring bonded to the nitrogen atom; with:

(ii) at least one monosubstituted derivative of the formula:

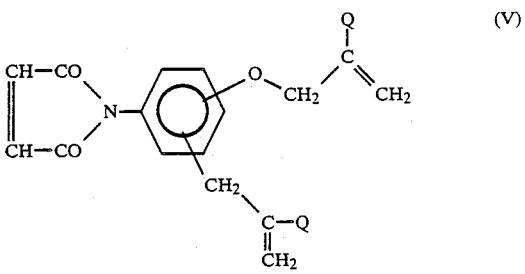

and, optionally, (iii) at least one disubstituted derivative of the formula:

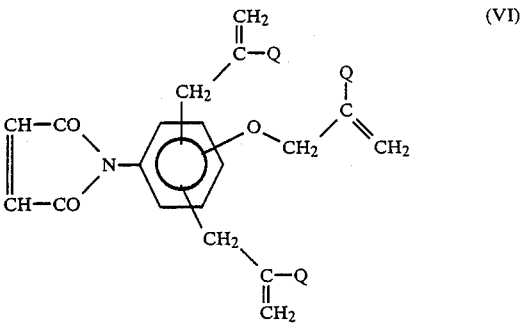

or (d₃) at least one substituted heterocyclic compound selected from vinyl pyridine, N-vinylpyrrolidone, allyl isocyanurate, triallyl isocyanurate and vinyl tetrahydrofuran and wherein Q in the above formulae (III), (IV), (V) and (VI) is —H or —CH₃.

* * * * *